United States Patent
Lee et al.

(10) Patent No.: US 11,712,192 B2
(45) Date of Patent: Aug. 1, 2023

(54) BIOMARKER FOR EARLY DETECTION OF ALZHEIMER DISEASE

(71) Applicant: National Cheng Kung University, Tainai (TW)

(72) Inventors: Gwo Giun Lee, Tainan (TW); Te-Han Kung, Taichung (TW); Tzu-Cheng Chao, Kaohsiung (TW); Yu-Min Kuo, New Taipei (TW); Meng-Ru Tsai, Chiayi (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 480 days.

(21) Appl. No.: 16/724,293

(22) Filed: Dec. 22, 2019

(65) Prior Publication Data
US 2021/0186409 A1   Jun. 24, 2021

(51) Int. Cl.
| A61B 5/00 | (2006.01) |
| G16H 30/40 | (2018.01) |
| G06N 20/00 | (2019.01) |
| A61B 5/055 | (2006.01) |
| A61B 5/16 | (2006.01) |

(52) U.S. Cl.
CPC .......... *A61B 5/4088* (2013.01); *A61B 5/0042* (2013.01); *A61B 5/055* (2013.01); *A61B 5/16* (2013.01); *A61B 5/7267* (2013.01); *G06N 20/00* (2019.01); *G16H 30/40* (2018.01); *A61B 2576/026* (2013.01)

(58) Field of Classification Search
CPC ..... A61B 5/4088; A61B 5/0042; A61B 5/055; A61B 5/7267; A61B 2576/026; A61B 5/7275; G06N 20/00; G16H 30/40
See application file for complete search history.

(56) References Cited

U.S. PATENT DOCUMENTS

| 8,452,373 B2 * | 5/2013 | Wyrwicz ............. A61B 5/4088 600/410 |
| 9,125,580 B2 | 9/2015 | Lee et al. |

OTHER PUBLICATIONS

Platero et al., "Discriminating Alzheimer's disease progression using a new hippocampal marker from T1-weighted MRI: The local surface roughness," (Oct. 19, 2018), Wiley Periodicals, Hum Brain Mapp. 2019;40:1666-1676. (Year: 2018).*

(Continued)

*Primary Examiner* — Joel Lamprecht
*Assistant Examiner* — Ashish S Jasani
(74) *Attorney, Agent, or Firm* — Rabin & Berdo, P.C.

(57) ABSTRACT

The present disclosure relates to a method for providing biomarker for early detection of Alzheimer's Disease (AD), and particularly to a method that is able to enhance the accuracy of predicting AD from Mild Cognitive Impairment (MCI) patients using the Hippocampus magnetic resonance imaging (MRI) scans and Mini-Mental State Examination (MMSE) data. The providing MRI images containing the anatomical structure of Hippocampus biomarker and MMSE data as a training data set; training a processor using the training data set, and the training comprising acts of receiving MRI images and MMSE data as a testing data set from a target; and classifying the test data by the trained processor to include aggregating predictions.

10 Claims, 7 Drawing Sheets

(56) References Cited

OTHER PUBLICATIONS

Raut et al.,"A machine learning based approach for detection of alzheimer's disease using analysis of hippocampus region from MRI scan," (Jul. 18, 2017) 2017 International Conference on Computing Methodologies and Communication (ICCMC), 2017, pp. 236-242. (Year: 2017).*

Kim et al., "Disentangling hippocampal shape anomalies in epilepsy," (Sep. 11, 2013) Front. Neurol., vol. 4, article 131, pp. 1-6. (Year: 2013).*

Fischl et al., "Whole Brain Segmentation: Automated Labeling of Neuroanatomical Structures in the Human Brain" (Jan. 31, 2002) Neuron 33, 341-355. (Year: 2002).*

Iglesias et al., "A computational atlas of the hippocampal formation using ex vivo, ultra-high resolution MRI: Application to adaptive segmentation of in vivo MRI," (Jul. 15, 2015), NueroImage, vol. 115, , pp. 117-137. (Year: 2015).*

Platero et al., "Longitudinal Neuroimaging Hippocampal Markers for Diagnosing Alzheimer's Disease," (May 21, 2018) Neuroinform 17, 43-61. (Year: 2018).*

Wisse et al., "A critical appraisal of the hippocampal subfield segmentation package in FreeSurfer," (Sep. 25, 2014) Front. Aging Neurosci. (Year: 2014).*

Dadar et al., "Acomparison of publicly available linear MRI stereotaxic registration techniques," (Jul. 1, 2018) NeuroImage vol. 174, pp. 191-200. (Year: 2018).*

Freesurfer Wiki <https://surfer.nmr.mgh.harvard.edu/fswiki/> (Year: NA) (Year: NA) (Year: NA) (Year: NA) (Year: NA) (Year: NA) (Year: NA) (Year: NA) (Year: NA) (Year: NA).*

Freesurfer Release Notes <https://surfer.nmr.mgh.harvard.edu/fswiki/ReleaseNotes> (Year: NA) (Year: NA) (Year: NA) (Year: NA) (Year: NA) (Year: NA) (Year: NA) (Year: NA) (Year: NA).*

Freesurfer HippocampalSubfields <https://surfer.nmr.mgh.harvard.edu/fswiki/HippocampalSubfields> (Year: NA) (Year: NA) (Year: NA) (Year: NA) (Year: NA) (Year: NA) (Year: NA) (Year: NA).*

Freesurfer Citations <https://surfer.nmr.mgh.harvard.edu/fswiki/FreeSurferMethodsCitation> (Year: NA) (Year: NA) (Year: NA) (Year: NA) (Year: NA) (Year: NA) (Year: NA) (Year: NA) (Year: NA).*

Freesurfer ColorLUT <https://surfer.nmr.mgh.harvard.edu/fswiki/FsTutorial/AnatomicalROI/FreeSurferColorLUT> (Year: 2015).*

Re: [Freesurfer] Cortical surface tessellation and smoothing <https://www.mail-archive.com/freesurfer@nmr.mgh.harvard.edu/msg05413.html> (Year: 2007).*

Freesurfer Support <https://surfer.nmr.mgh.harvard.edu/fswiki/FreeSurferSupport> (Year: NA) (Year: NA) (Year: NA) (Year: NA) (Year: NA) (Year: NA) (Year: NA) (Year: NA).*

Freesurfer IntensityNormalization <https://surfer.nmr.mgh.harvard.edu/fswiki/IntensityNormalization> (Year: 2008).*

Freesurfer Normalization <https://surfer.nmr.mgh.harvard.edu/fswiki/normalization> (Year: 2009).*

Freesurfer Normalization2 <https://surfer.nmr.mgh.harvard.edu/fswiki/normalization2> (Year: 2009).*

Freesurfer Talairach <https://surfer.nmr.mgh.harvard.edu/fswiki/talairach> (Year: 2009).*

Freesurfer MRL_mask <https://surfer.nmr.mgh.harvard.edu/fswiki/mri_mask> (Year: 2018).*

Dalton et al., "Segmenting subregions of the human hippocampus on structural magnetic resonance image scans: An illustrated tutorial," (Apr. 6, 2017) Brain Neurosci Adv. Dec.-Jan. 2017; 1:2398212817701448. (Year: 2017).*

Shi et al., "Hippocampal subfields segmentation in brain MR images using generative adversarial networks," (Jan. 21, 2019) BioMedical Engineering Online vol. 18, Article No. 5. (Year: 2019).*

DeKraker et al., "Unfolding the hippocampus: an intrinsic coordinate system for subfield segmentations and quantitative mapping", (Jun. 7, 2017) bioRxiv 146878. (Year: 2017).*

* cited by examiner

BIOMARKER FOR EARLY DETECTION OF ALZHEIMER DISEASE

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent Office patent file or records, but otherwise reserves all copyright rights whatsoever.

FIELD OF THE INVENTION

The present disclosure relates to a method for predicting Alzheimer's Disease (AD), and particularly to a method that is able to enhance the accuracy of predicting AD from Mild Cognitive Impairment (MCI) patients by providing biomarker.

BACKGROUND OF THE INVENTION

Cognitive decline is one of the most concerning behavioral symptoms such as AD. Seamless changes in the AD continuum take years if not decades to progress from normal cognition (NC) to MCI, with gradual evolution of clinically probable AD to confirmed AD. Early detection and accurate diagnosis of AD require careful medical assessment, including patient history as well as physical and neurological examinations.

The MMSE is a brief cognitive assessment tool commonly used to screen for dementia. Neuroimaging modalities such as MRI that provides biologic evidences which cognitive decline is neurodegenerative as they contain detailed information regarding the subcortical structures, good contrast of the gray matter, and the integrity of the brain tissue.

Machine learning techniques have been widely used over the past few years for the analysis of biomedical images, and more particularly to frameworks known as deep learning, which is based on artificial neural networks, which has received increased attention because of its remarkable success in predicting various clinical outcomes of interest. The convolutional neural network (CNN) models are considered to be efficient deep learning techniques for object recognition and classification.

However, MRI scans are characterized as complex, unstructured data structures and thus require sophisticated means by which to perform an efficiently quantitative analysis. The most common neurological examination for predicting AD is to monitor the overall volume of Hippocampus from MRI scans.

Accordingly, there's a need to combined the structural information derived from neuroimaging data (i.e., MRI scans) and functional information (i.e., MMSE) derived from screening tools and cognitive assessment methods can result in a better combined metric of predicting AD.

SUMMARY

According to an aspect of the present invention, a method for predicting AD is provided to create a predictive model of AD by considering detailed structural and anatomic information contained within the MRI images as well as cognitive function assessed using the MMSE.

According to an embodiment of the present invention, the method for predicting Alzheimer's Disease comprising acts providing MRI images containing the anatomical structure of Hippocampus and MMSE data as a training data set; training a processor using the training data set; receiving MRI images and MMSE data as a testing data set from a target; and classifying the test data by the trained processor to include aggregating predictions.

The training comprising acts of proceeding an MRI image preprocessing to determine volume of a Hippocampus of each MRI images, and segmenting the Hippocampus into sections; determining surface areas for each section of each Hippocampus in MRI images; determining a Ratio of Principle Curvature (RPC) for each section of each Hippocampus; and selecting candidate parameters as inputs to iteratively train an iterative neural network in the processor, wherein the candidate parameters are selected from the volume of Hippocampus, the surface areas and the PRC of sections of Hippocampus, and scores of MMSE data.

According to an aspect of the present invention, a method quantifying the anatomical structure of a Hippocampus is provided, which segments the Hippocampus into sections and quantifies them into biomarkers (factoring features) for predicting Alzheimer's Disease.

According to an embodiment of the present invention, the method for quantifying the anatomical structure of a Hippocampus comprising acts of receiving MRI images of a brain scan; preprocessing the MRI images to identify the Hippocampus for determining volumes of each identified Hippocampus; segmenting each identified Hippocampus into multiple sections; reconstructing the each identified Hippocampus with sections to build a 3D Hippocampus model; smoothing the surface area of the 3D Hippocampus model; calculating a surface area of each sections of each identified Hippocampus; and calculating a maximum curvature and a minimum curvature of each sections of each identified Hippocampus to determine an RPC.

BRIEF DESCRIPTION OF THE DRAWINGS

Embodiments of the invention are described in more details hereinafter with reference to the drawings, in which.

DETAILED DESCRIPTION

In the following description, For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of particular elements, the term "includes/comprises" means includes but not limited to, the term "including/comprising" means including but not limited to, and the term "based on" means based at least in part on.

Figure 1:
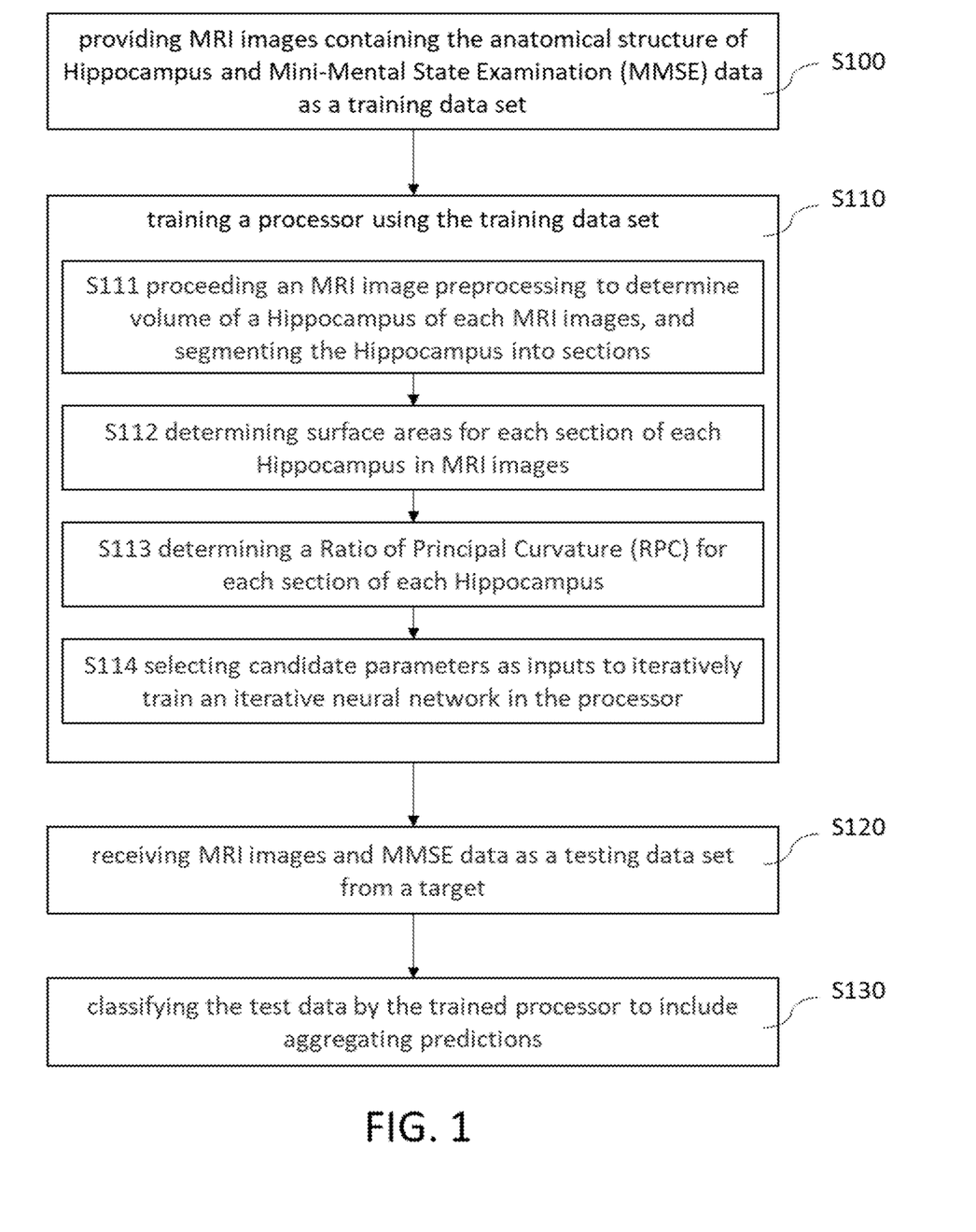
FIG. 1 is a flowchart illustrating a method for predicting Alzheimer's Disease (AD) in accordance with an embodiment of the present invention.
Figure 2:
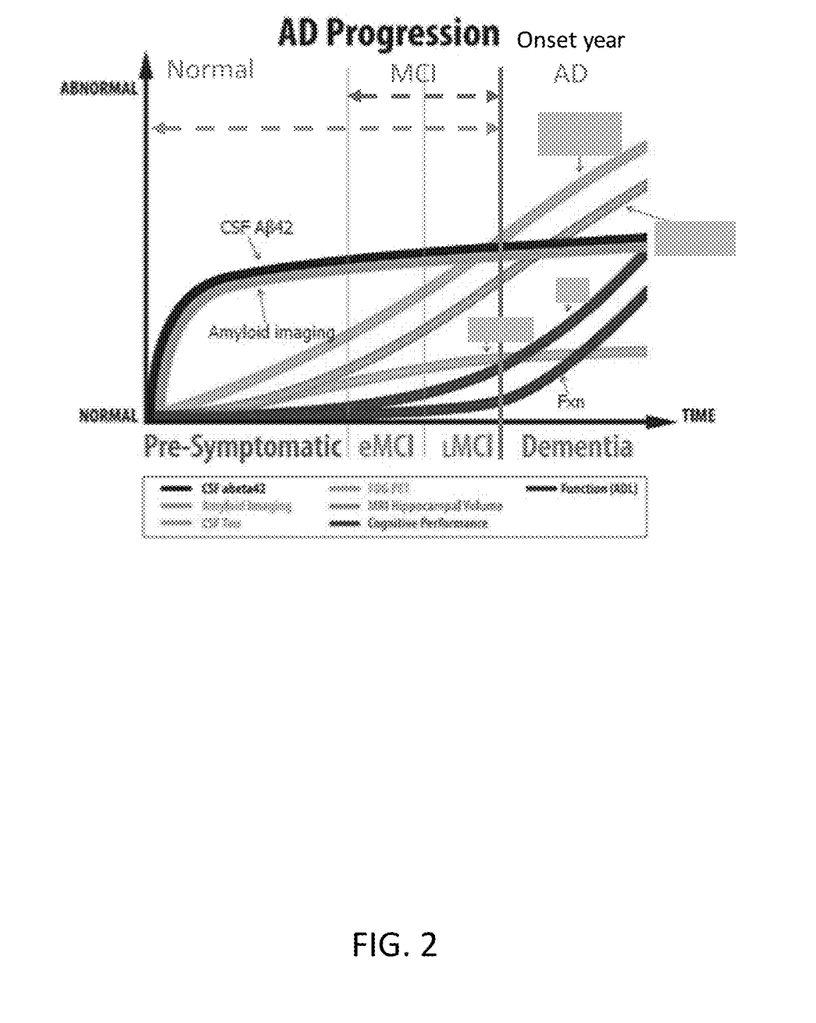
FIG. 2 is an exemplary diagram illustrating the observing factors in the AD progression.

With reference to FIGS. 1 and 2, FIG. 1 is a flowchart illustrating a method for predicting AD in accordance with an embodiment of the present invention; and FIG. 2 is an exemplary diagram illustrating the observing factors in the AD progression. As shown in FIG. 2, the Hippocampus volume is considered the most important and crucial factor to distinguish individuals with AD, especially from the ones who have MCI is crucial within the realm of early detection of AD.

The objective of the present invention is to create a predictive computing model of AD by considering detailed structural and anatomic information contained within the MRI images as well as cognitive function assessed using the MMSE.

Accordingly, as shown in FIG. 1, in an embodiment, A method for predicting Alzheimer's Disease comprising acts of S100 providing MRI images containing the anatomical structure of Hippocampus and MMSE data as a training data set, S110 training a processor using the training data set, S120 receiving MRI images and MMSE data as a testing data set from a target, and S130 classifying the test data by the trained processor to include aggregating predictions.

The acts of S110 training of the processor using the training data set is comprising acts of S111 proceeding an MRI image preprocessing to determine volume of a Hippocampus of each MRI images, and segmenting the Hippocampus into sections, S112 determining surface areas for each section of each Hippocampus in MRI images, S113 determining a Ratio of RPC for each section of each Hippocampus, and S114 selecting candidate parameters as inputs to iteratively train an iterative neural network in the processor. the candidate parameters are selected from the volume of Hippocampus, the surface areas and PRC of sections of Hippocampus, and scores of the MMSE data.

Figure 3A:
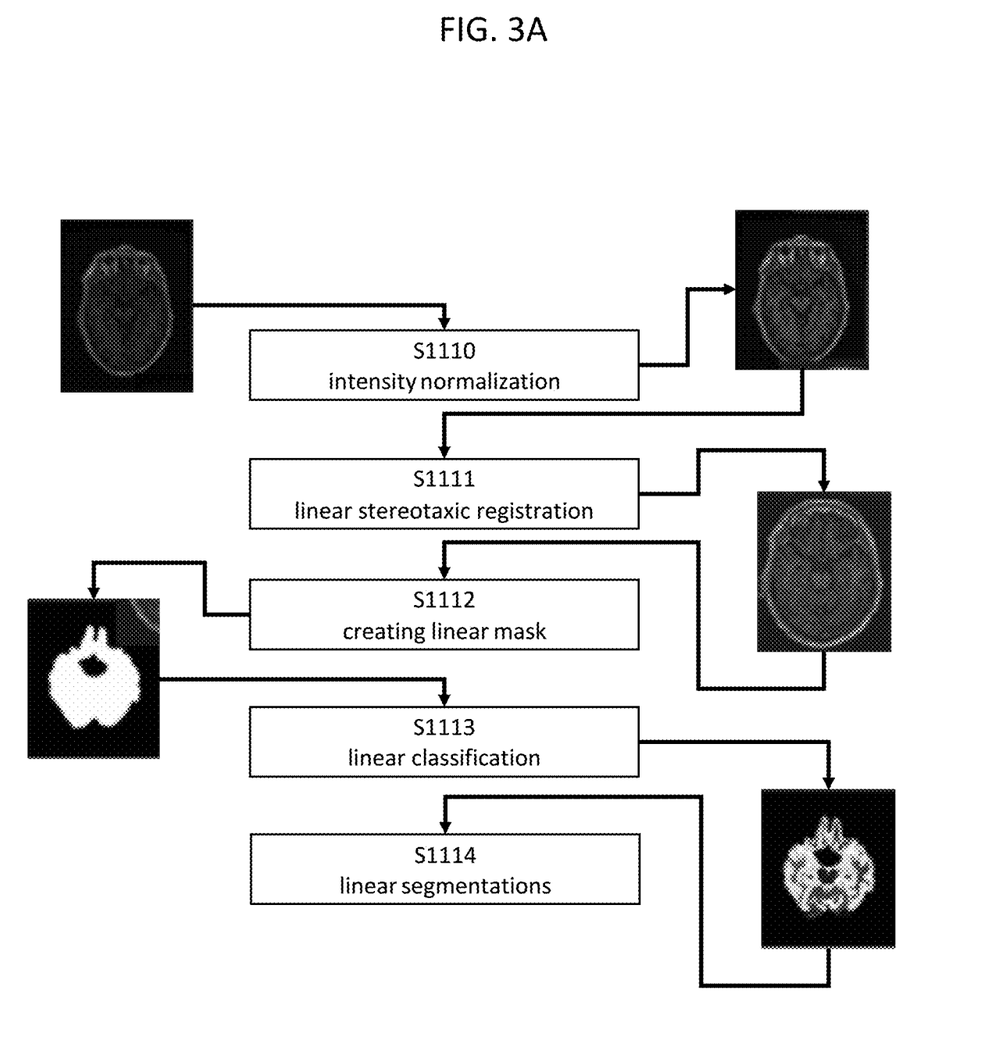
FIG. 3A is a flowchart illustrating the acts of S111 with corresponding MRI images for each of steps in accordance with an embodiment of the present invention.
Figure 3B:
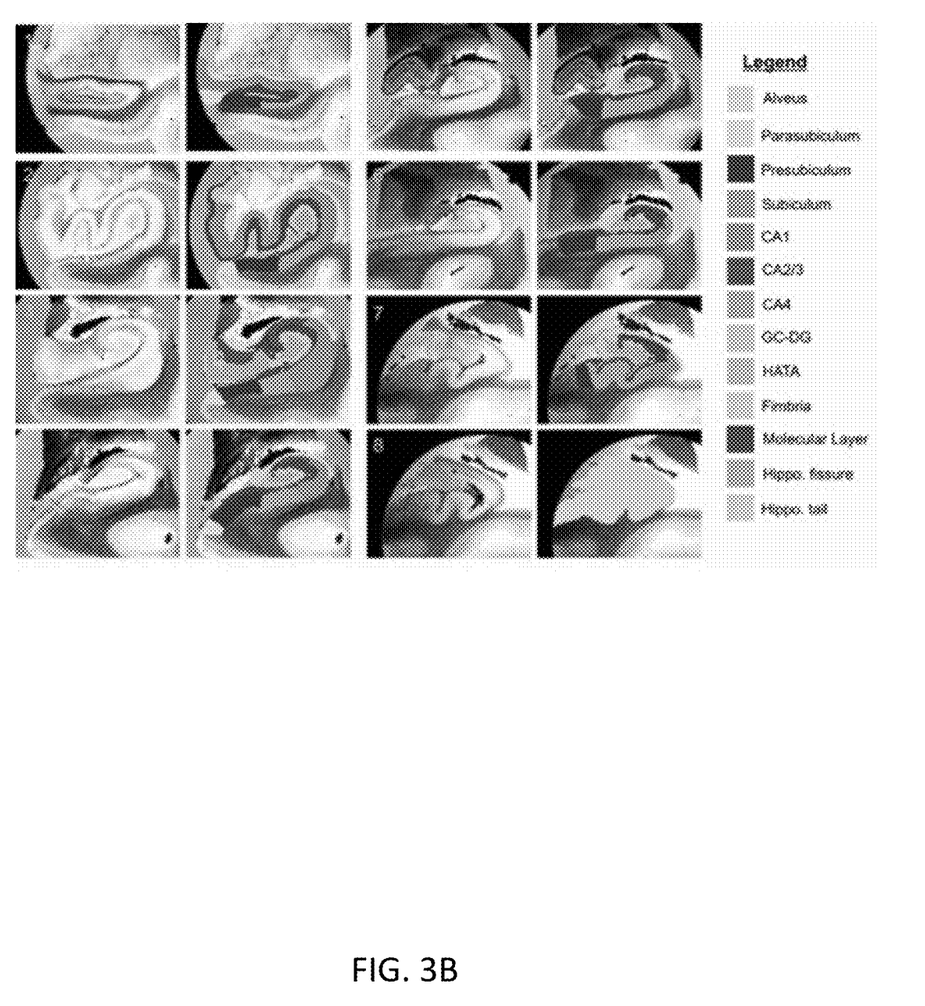
FIG. 3B is an exemplary diagram illustrating the sections of the Hippocampus.

With further reference to FIGS. 3A and 3B, FIG. 3A is a flowchart illustrating the acts of S111 with corresponding MRI images for each of steps in accordance with an embodiment of the present invention; and FIG. 3B is an exemplary diagram illustrating the sections of the Hippocampus. As shown in FIG. 3A, in this embodiment, the MRI image preprocessing S111 comprising acts of S1110 an intensity normalization, S1111 linear stereotaxic registration, S1112 creating linear mask, S1113 linear classification and S1114 linear segmentations.

In the present disclosure, the acts of S1110 to S1114 for preprocessing and segmenting the MRI images is proceed by a computer using FreeSurfer. FreeSurfer is a software for the analysis and visualization of structural and functional neuroimaging data from cross-sectional or longitudinal studies. It is developed by the Laboratory for Computational Neuroimaging at the Athinoula A. Martinos Center for Biomedical Imaging at Massachusetts General Hospital. For structural MRI image, FreeSurfer provides a cortical and subcortical full processing pipeline describing as following:

1. Intensity correction, noise filtering, artifact correction, skull stripping and gray-white matter segmentation;
The surface-based stream
2. Reconstruction of cortical surface models (gray-white boundary surface);
3. Nonlinear registration of the cortical surface of an individual with a stereotaxic atlas (MNI305 atlas);
The volume-based stream
4. Labeling of cortical regions and subcortical regions;
5. Statistical analysis of group morphometry differences; and
6. Subfields of Hippocampus segmentation.

Therefore, the volume and the sections of Hippocampus is able to obtained by using the MRI image through FreeSurfer. As shown in FIG. 3B, the sections of Hippocampus at least comprise alveus, parasubiculum, presubiculum, subiculum, CA1, CA2/3, CA4, GC-DG, HATA, fimbria, molecular layer, Hippocampus fissure and Hippocampus tail.

Figure 4A:
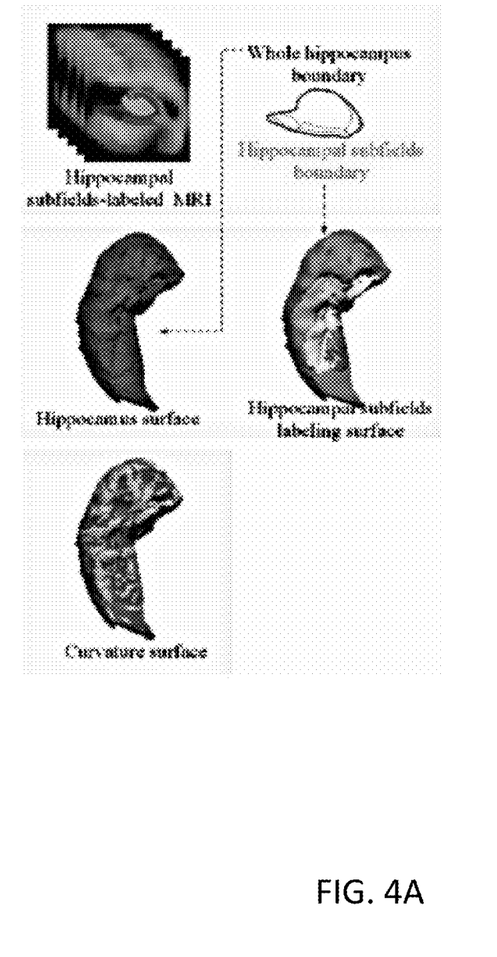
FIG. 4A is an exemplary diagram of a 3D Hippocampus model in accordance with an embodiment of the present invention.
Figure 4B:
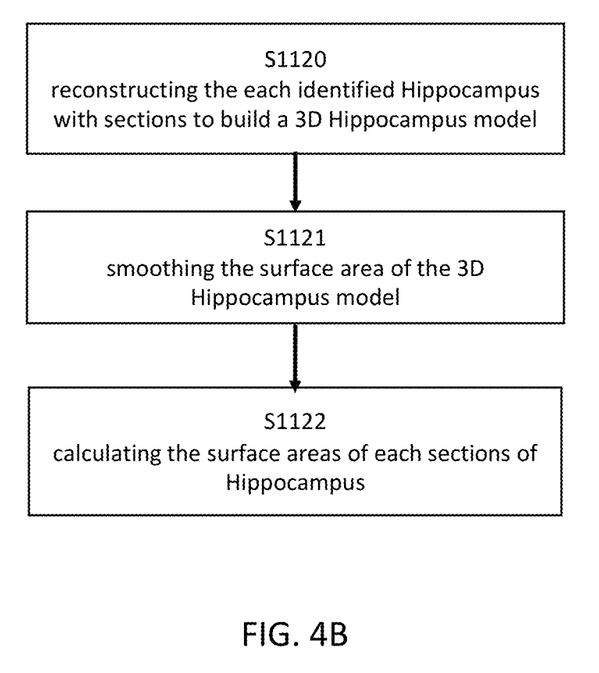
FIG. 4B is a flowchart illustrating the step of S112 in accordance with an embodiment of the present invention.

With reference to FIGS. 4A and 4B, FIG. 4A is an exemplary diagram of a 3 Dimensions (3D) Hippocampus model in accordance with an embodiment of the present invention; and FIG. 4B is a flowchart illustrating the step of S112 in accordance with an embodiment of the present invention. In act of S112, the Hippocampus is built in a 3D Hippocampus model with each identical section. In this embodiment, the 3D Hippocampus model is built by Marching cubes. The "marching cubes" described here is the technique directing to a patent, U.S. Pat. No. 4,710,876 "System And Method For The Display Of Surface Structures Contained Within The Interior Region Of A Solid Body" by Harvey E. Cline and William E. Lorensen, issued on Dec. 1, 1987.

As shown in FIG. 4A, a block of volumetric data is displayed, it determines interfaces between adjacent data values indicating a change in the measured value, and then models the surfaces with triangular elements having a vector normal to the surface at each of the vertices of the triangle. Laplacian smoothing is then applied to the 3D Hippocampus model which is configured for improving the quality of the triangulation while remaining faithful to the original surface geometry. The Hippocampus surface and each surface areas of the sections are obtained after the surface smoothing. Therefore, as shown in FIG. 4B, the act of 112 further comprises acts of S120 reconstructing the each identified Hippocampus with sections to build a 3D Hippocampus model, S1121 smoothing the surface area of the 3D Hippocampus model; and S122 calculating the surface areas of each sections of Hippocampus.

In act of S113, a curvature analysis to the 3D Hippocampus model is proceeded to determine an average of a Ratio of Principle Curvature (RPC) for each section of each hippocampus. During the calculation of curvature, maximum curvatures and minimum curvatures of each sections are calculated, wherein the average of RPC is $$RPC_{avg}=SUM(\text{maximum curvature})/SUM(\text{minimum curvature})$$

Figure 5:
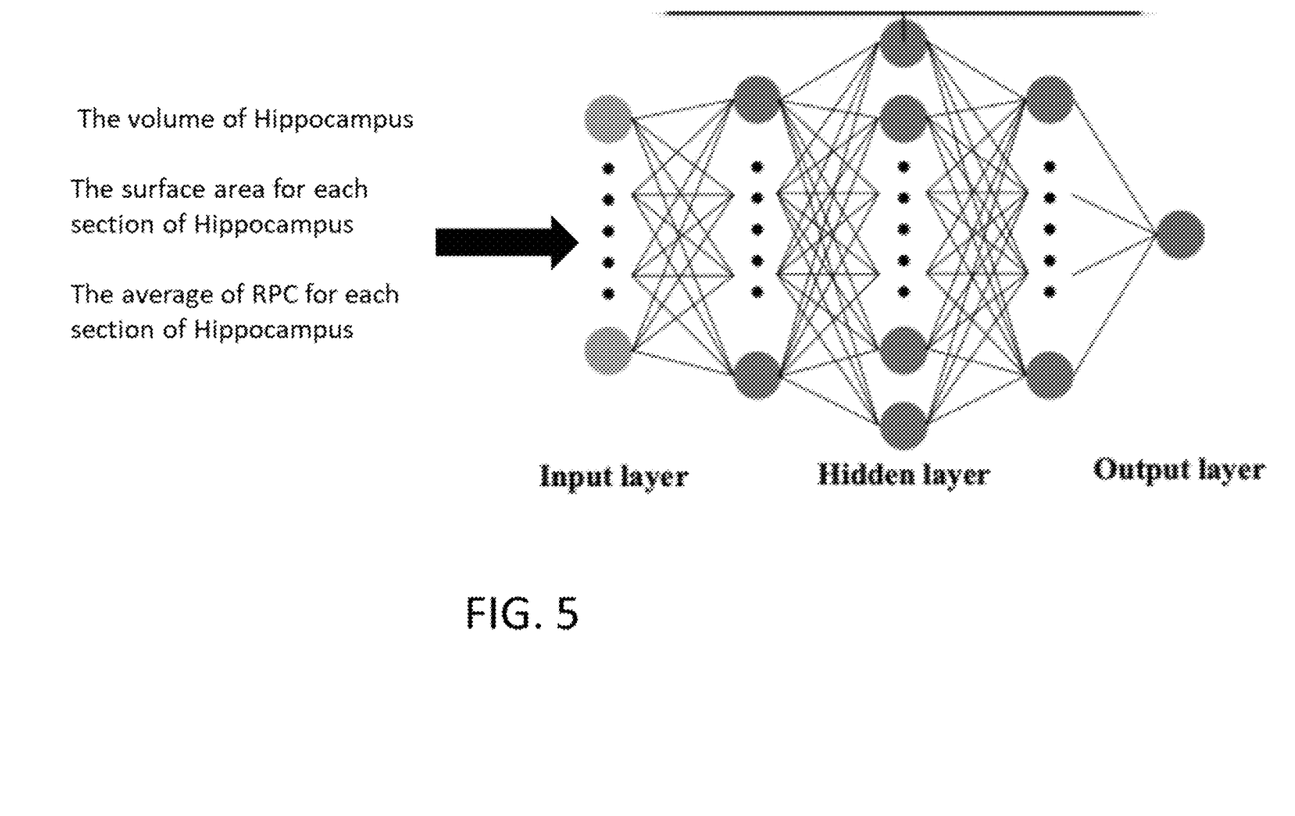
FIG. 5 is an exemplary diagram of an iterative neural network in accordance with an embodiment of the present invention.

With reference to FIG. 5, FIG. 5 is an exemplary diagram of an iterative neural network in accordance with an embodiment of the present invention. As describe in above, the volume, average of curvature for each section, and surface of the Hippocampus are obtained. These values are considered to be candidate parameters as inputs for the iterative neural network. As shown in FIG. 5, there're multiple input nodes, at least one output node and multiple layers of neuron nodes between the input and the output.

According to inventor's experiments, in an prefer embodiment, the values of Hippocampus volume, Subiculum surface area, CA1 surface area, CA3 surface area, and the average RPCs of Subiculum, CA1 and CA3 are selected to be the candidate parameters. In contrast, unlikely conventional studies only relied on the volume of the Hippocampus, the present invention uses curvatures to quantify the Hippocampus as features.

Besides neurological examinations, in order to enhance the accuracy of prediction, especially for predicting AD from MCI patients, the present invention further uses physical/cognitive function assessed using MMSE data to train the iterative neural network. the parameters both in MRI images and MMSE data can be used in a single machine learning model, or separately into two individual models. As a person skilled in the art will realize that for separating models, the results can be combined later using the majority voting.

The MMSE is a brief cognitive assessment tool commonly used to screen for dementia. The MMSE is composed of 11 major items forming a 30-point questionnaire with five different domains of cognition analyses. The five domains are (1) Orientation, contributing a maximum of 10 points, (2) Memory/Recall, contributing a maximum of 6 points, (3) Attention and calculation, as a measure of working memory, contributing a maximum of 5 points, (4) Language, contributing a maximum of 8 points, and (5) Design copying, contributing a maximum of 1 point. The 11 items are temporal orientation (5 points), spatial orientation (5 points), immediate memory (3 points), attention/concentration (5 points), delayed recall (3 points), naming (2 points), verbal repetition (1 points), verbal comprehension (3 points), writing (1 points), reading a sentence (1 points), and constructional praxis (1 points). In general, the MMSE was administered and scored by a medical doctor certified in internal-medicine with extensive dementia experience.

Accordingly, the scores of MMSE data are used as candidate parameters for additional inputs. Based on inventor's experiment, orientation, attention, recall and language are the most effective features for accuracy.

Below three tables shows the accuracy results of predicting AD with different inputs in iterative neural networks. In this embodiment, a basic Multilayer Perceptron (MLP) architecture is used with numerous of hidden layers. Table I uses only neuropsychological data (i.e., the MMSE score) as parameters. The accuracy is between 67.78% to 72.22%. Table II uses only neuroimaging features (i.e., the volume, surface area and RPC of the Hippocampus) as parameters. The accuracy is between 67.16% to 72.65%. Table III is combination of the neuropsychological data and neuroimaging feature data. The accuracy is between 75.12% to 75.86%.

TABLE I

| Input feature Basic MLP architecture | | | Neuropsychological data 2 hidden layers with 4 neurons | | |
| --- | --- | --- | --- | --- | --- |
| Selection method | Neuro-psychological test | Number of Features | Accuracy | Sensitivity | Specificity |
| Univariate selection | MMSE | 4 | 72.22% | 70.37% | 74.07% |
| Feature importance | MMSE | 2 | 67.78% | 57.04% | 78.52% |

TABLE II

| Input feature Basic MLP architecture | | | Neuroimaging features 2 hidden layers with 12 neurons | | |
| --- | --- | --- | --- | --- | --- |
| Selection method | Criteria | Number of features | Accuracy | Sensitivity | Specificity |
| Univariate selection | p-value < 0.01 | 11 | 67.16% | 70.00% | 64.32% |
| Univariate selection | p-value < 0.05 | 19 | 71.17% | 69.38% | 72.96% |
| Univariate selection | p-value < 0.1 | 25 | 69.26% | 70.99% | 67.53% |
| Feature importance | Random forest Top 10 | 10 | 67.59% | 68.02% | 67.16% |
| Feature importance | Random forest Top 15 | 15 | 71.91% | 69.75% | 74.07% |
| Feature importance | Random forest Top 20 | 20 | 72.65% | 71.48% | 73.83% |
| Feature importance | Random forest Top 25 | 25 | 71.54% | 69.01% | 74.07% |

TABLE III

| Input feature Basic MLP architecture | | | Neuroimaging + neuropsychological data 2 hidden layers with 15 neurons | | |
| --- | --- | --- | --- | --- | --- |
| Criteria | Neuro-psychological test ($Univariate\ selection$) | Number of feature | Accuracy | Sensitivity | Specificity |
| Univariate selection method | | | | | |
| p-value < 0.05 | MMSE | 23 | 75.86% | 74.07% | 77.65% |
| p-value < 0.1 | MMSE | 29 | 73.95% | 72.10% | 75.80% |
| Feature importance method (Random forest classifier) | | | | | |
| Random forest Top 15 | MMSE | 19 | 75.12% | 76.05% | 74.20% |
| Random forest Top 20 | MMSE | 24 | 75.56% | 74.94% | 76.17% |

Accordingly, the present invention combines the structural information derived from functional information and neuroimaging data that is derived from quantifying the anatomical structure of a Hippocampus which achieves better accuracy of predicting AD.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

The invention claimed is:

1. A method of providing biomarker for early detection of Alzheimer's Disease, comprising:
   providing magnetic resonance imaging (MRI) images containing the anatomical structure of Hippocampus and Mini-Mental State Examination (MMSE) data as a training data set;
   training a processor using the training data set, and the training comprising acts of
      proceeding an MRI image preprocessing to determine volume of each Hippocampus in MRI images, and segmenting each Hippocampus into sections;
      determining surface areas for each section of each Hippocampus in MRI images;
      determining an average of Ratio of Principal Curvature (RPC) for each section of each Hippocampus, wherein the average of RPC for each section of each Hippocampus is a ratio of SUM(maximum curvature) and SUM(minimum curvature) for each section of each Hippocampus; and
      selecting candidate parameters as inputs to iteratively train an iterative neural network in the processor, wherein the candidate parameters comprise the volume of Hippocampus, the surface area and the average of the RPC for each section of Hippocampus, and scores of MMSE data;
   receiving MRI images and MMSE data as a testing data set from a target; and
   classifying the testing data set by the trained processor to include aggregating predictions.

2. The method as claimed in claim 1, wherein the act of proceeding an MRI image preprocessing to determine volume of each Hippocampus in MRI images and segmenting each Hippocampus into sections, comprises an intensity normalization, linear stereotaxic registration, creating linear mask, linear classification and linear segmentations.

3. The method as claimed in claim 2, wherein the segmentations of the Hippocampus are alveus, parasubiculum, presubiculum, subiculum, CA1, CA2/3, CA4, GC-DG, HATA, fimbria, molecular layer, Hippocampus fissure and Hippocampus tail.

4. The method as claimed in claim 3, wherein the candidate parameter comprises values of Hippocampus volume, Subiculum surface area, CA1 surface area, CA3 surface area, an average of RPC for Subiculum, an average of RPC for CA1, and an average of RPC for CA3.

5. The method as claimed in claim 1, wherein the candidate parameter comprises scores of orientations, attention, recall and language in the MMSE data.

6. The method as claimed in claim 1, wherein the act of classifying the MRI images and MMSE data by the trained processor are proceed in different iterative neural networks.

7. The method as claimed in claim 1, wherein the acts of preprocessing and segmenting the MRI images are performed by a computer using FreeSurfer.

8. The method as claimed in claim 1, wherein the act of determining surface areas for each section of each Hippocampus in MRI images comprises acts of reconstructing the each identified Hippocampus with sections to build a 3 Dimensions (3D) Hippocampus model, smoothing the surface area of the 3D Hippocampus model; and calculating the surface areas of each section of Hippocampus.

9. The method as claimed in claim 8, wherein the 3D Hippocampus model is built by Marching cubes.

10. The method as claimed in claim 8, wherein the act of smoothing the surface area of the 3D Hippocampus model is achieved by Laplacian smoothing.

* * * * *